United States Patent
Wood et al.

(10) Patent No.: US 10,458,914 B2
(45) Date of Patent: *Oct. 29, 2019

(54) METHOD AND SYSTEM FOR RAPID PARASITE DETECTION

(71) Applicants: Monash University, Clayton (AU); University of Melbourne, Parkville (AU)

(72) Inventors: Bayden Robert Wood, Upwey (AU); Aazam Khoshmanesh, Mount Waverley (AU); Matthew Dixon, Brunswick West (AU); Leann Tilley, North Melbourne (AU); Donald McNaughton, Ashburton (AU)

(73) Assignees: Monash University, Clayton (AU); University of Melbourne, Parkville (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/988,995

(22) Filed: May 24, 2018

(65) Prior Publication Data

US 2018/0266948 A1    Sep. 20, 2018

Related U.S. Application Data

(63) Continuation of application No. 15/117,149, filed as application No. PCT/AU2014/000080 on Feb. 5, 2014, now Pat. No. 9,983,130.

(51) Int. Cl.
*G01J 5/00* (2006.01)
*G01N 21/552* (2014.01)
(Continued)

(52) U.S. Cl.
CPC ....... *G01N 21/552* (2013.01); *G01N 21/3577* (2013.01); *G01N 33/49* (2013.01);
(Continued)

(58) Field of Classification Search
CPC .... G01N 21/35; G01N 21/3577; G01N 33/49; G01N 2021/3595; G01N 2201/129; G01N 21/552
See application file for complete search history.

(56) References Cited

U.S. PATENT DOCUMENTS

2012/0225019 A1*  9/2012  Peak ................... G01N 33/5085
                                                               424/9.2
2017/0073725 A1*  3/2017  Upton ...................... C12Q 1/18

OTHER PUBLICATIONS

Sharma et al., "Design considerations for surface plasmon resonance based detection of human blood group in near infrared," 2010, Journal of Applied Physics, vol. 107, pp. 034701-10 to 304701-7 (Year: 2010).*

* cited by examiner

*Primary Examiner* — Kiho Kim
(74) *Attorney, Agent, or Firm* — Dorsey & Whitney LLP

(57) ABSTRACT

The invention described herein relates to a method of detecting malaria comprising the steps of: (i) delivering an evanescent IR beam through said ATR substrate in contact with a patient blood sample; (ii) detecting IR radiation transmitted from the ATR substrate to produce a signal characteristic for one or more lipids in the sample, and (iii) processing said signal and a set of reference library spectra of lipids associated with malaria parasites in order to detect matches and quantify said one or more lipids in the sample. In contrast to the prior art, the present invention relies on detecting lipids instead of hemozoin.

24 Claims, 8 Drawing Sheets

(51) Int. Cl.
*G01N 21/3577* (2014.01)
*G01N 33/49* (2006.01)
*G01N 21/35* (2014.01)
(52) U.S. Cl.
CPC ................ *G01N 2021/3595* (2013.01); *G01N 2201/129* (2013.01)

METHOD AND SYSTEM FOR RAPID PARASITE DETECTION

CROSS REFERENCE TO RELATED APPLICATIONS

The present application is continuation of U.S. application Ser. No. 15/117,149, filed on Aug. 5, 2016, now U.S. Pat. No. 9,983,130, which is a U.S. National Phase of International Patent Application Serial No. PCT/AU2014/000080, entitled "METHOD AND SYSTEM FOR RAPID MALARIA DETECTION", filed on Feb. 5, 2014, the entire contents of which are hereby incorporated by reference in their entirety for all purposes.

FIELD OF USE

The present invention relates to the field of malaria detection, particularly detection and quantification of early stage malaria parasites in infected cells.

In one form, the invention relates to a method of using Attenuated Total Reflection Infrared (ATR-IR) spectroscopy for detection and quantification of malaria.

In another form, the invention relates to a method of multivariate analysis for analysis of data obtained by ATR-IR.

In one particular aspect the present invention is suitable for use for diagnosis of malarial infection.

It will be convenient to hereinafter describe the invention in relation to field use of the present invention, however it should be appreciated that the present invention is not limited to that use only and the present invention can be adapted for use in a range of locations including laboratories, and in a range of sizes from bench scale high throughput diagnostic machines of the type used in commercial pathology laboratories.

BACKGROUND

Throughout this specification the use of the word "inventor" in singular form may be taken as reference to one (singular) inventor or more than one (plural) inventor of the present invention.

It is to be appreciated that any discussion of documents, devices, acts or knowledge in this specification is included to explain the context of the present invention. Further, the discussion throughout this specification comes about due to the realisation of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

Attenuated Total Reflection Infrared (ATR-IR) Spectroscopy

Spectroscopy is the branch of science devoted to discovering the chemical composition of materials by examining the interaction of electromagnetic radiation with the material. Infrared (IR) spectroscopy relates primarily to the absorption of energy by molecular vibrations having wavelengths in the infrared segment of the electromagnetic spectrum, that is energy of wave number between 200 and 4000 $cm^{-1}$. Raman spectroscopy relates to the inelastic scattering of monochromatic light giving wavelength shifts that depend on the molecular vibrations, having typically wave number shifts between 20 and 4000 $cm^{-1}$.

ATR is a sampling technique that can be used in conjunction with IR. ATR spectroscopy offers the advantages of being potentially portable, it is inexpensive and thus has become a very powerful tool in the analysis of biological cells and tissues. ATR also allows samples to be examined directly in the solid or liquid state without further preparation, and compared with transmission-IR, the path length into the sample is shorter, avoiding strong attenuation of the IR signal in highly absorbing media such as aqueous solutions.

In use, the sample is put in contact with the surface of a crystal having a higher refractive index than the sample. A beam of IR light is passed through the ATR crystal in such a way that it reflects at least once off the internal surface in contact with the sample. This reflection forms an evanescent wave which extends into the sample. The penetration depth into the sample depends on the wavelength of light, the angle of incidence and the indices of refraction for the ATR crystal and the medium being probed. The number of reflections may be varied. The beam is then collected by a detector as it exits the crystal.

Malaria

Malaria is a mosquito borne disease caused by parasitic protozoans of the genus *Plasmodium*. Five species of *Plasmodium* can infect humans—*P. falciparum, P. vivax, P. ovale, P. malariae* and *P. knowlesi*—but the vast majority of deaths are caused by *P. falciparum. P. falciparum* causes up to 1.2 million fatalities per annum. Accurate and early diagnosis followed by the immediate treatment of the infection is essential to reduce mortality and prevent overuse of antimalarial drugs.

New technologies to diagnose malaria must be cost effective and have high sensitivity and be able to detect circulating stages of the malaria parasite namely the ring and gametocyte forms because these are the only stages present in peripheral blood circulation.

The current suite of malarial diagnostics in clinical use include: (i) optical microscopy of thick blood films, (ii) Rapid Diagnostic Tests (RDTs) based on the detection of antigens specific to *P. falciparum*, (iii) gene amplification techniques such as polymerase chain reaction (PCR) and (iv) serological detection tests using antibodies such as immunofluorescence (IFA) and enzyme-linked immunosorbent assay (ELISA).

Each method has its own advantages and disadvantages. For example, optical microscopy requires preparation of blood smear samples using reagents and is based on visual assessment of the morphology of blood cells. The method is inherently subjective and requires experienced microscopists to make diagnosis.

Polymerase chain reaction (PCR) is considered the most sensitive and specific method, but has the drawbacks of being time consuming, technically sophisticated, expensive, and requiring a PCR machine, and is thus not suitable for malaria diagnosis in remote areas. Malaria RDTs, which are based on capture of parasite antigens by monoclonal antibodies incorporated into a test strip, are easy to use but are unable to quantify parasitemia.

A review of existing methods indicates that the examination of stained blood smears by light microscopy remains the method of choice for malaria diagnosis because it is inexpensive and has good sensitivity (5-10 parasites/µl blood). However, it is labor-intensive, lengthy, and more importantly, requires skilled and experienced microscopists, and is increasingly burdensome as malaria rates decline with most smears examined being negative.

During the course of its life the malaria parasite transgresses through several developmental stages including a sexual and an asexual reproductive pathway. The sexual or progeny phase, which occurs within the gut of female Anopheles mosquito, produces numerous infectious forms known as sporozoites that are transferred to the mosquito salivary glands and injected into the human host during a blood meal.

Sporozoites that enter a blood vessel move to the liver and invade hepatocytes where they develop into schizonts each containing tens of thousands of merozoites. The merozoites are subsequently released and invade the erythrocytes initiating the intraerythrocytic asexual phase of the life cycle. The merozoites grow and divide in the food vacuole and progress through three distinct morphological phases known as the ring, trophozoite and schizont stages (FIG. 1).

Mature stage parasites adhere to the vascular endothelium and thus only ring stage parasites are observed in blood smears. The schizonts burst, releasing the merozoites and the intraerythocytic cycle continues. Instead of replicating, some merozoites in the erythrocytes develop into sexual forms of the parasite, called male and female gametocytes, that are capable of undergoing transmission to mosquitoes.

Early stage gametocytes sequester away from the peripheral circulation but late stage gametocytes are present in blood smears, and gametocyte carriage underpins endemicity of disease. The detection of the rings in peripheral blood is critical for early diagnosis and treatment. The detection of low levels of gametocytes in asymptomatic long-term malaria carriers is critical to efforts to eradicate malaria.

During the intraerythrocytic stages of the parasites life cycle *P. falciparum* endocytoses packets of host cell cytoplasm, catabolizes the lipids and hemoglobin and in the process releases free heme, which is toxic to the organism. The malaria parasite has evolved a detoxification pathway that uses the lipid by-products to catalyze the sequestration of free heme into an insoluble pigment known as hemozoin (Hz). Hence Hz is a disposal product formed from the digestion of blood by malaria parasites (and some other blood feeding parasites).

Synchrotron powder diffraction analyses have shown that crystals of Hz (and its synthetic equivalent β-hematin) are composed of a repeating array of iron-carboxylate interacting heme dimers, stabilized by hydrogen bonding and π-π interactions.

Vibrational spectroscopic techniques have been used extensively in understanding the molecular and electronic structure of β-hematin and Hz; however, the use of vibrational spectroscopy for malaria diagnostics has not been fully exploited. Raman imaging microscopy has been explored as a potential non-subjective method to diagnose malaria parasites based on the strong scattering from the Hz pigment. (Wood et al, *Resonance Raman microscopy in combination with partial dark-field microscopy lights up a new path in malaria diagnostics*, Analyst 2009, 134. 1119-1125). While the technique has shown potential to detect ring forms of the parasite the time taken to record an image is on the order of several hours and therefore not suitable for the clinical environment.

Efforts have also been made to investigate the potential of synchrotron Fourier Transform Infrared (FTIR) in combination with Principal Component Analysis (PCA) to differentiate between intraerythrocytic stages of the parasite life cycle based on the molecular signatures of Hz and specific lipids (Webster et al. *Discriminating the Intraerythrocytic Lifecycle Stages of the Malaria Parasite Using Synchrotron FT-IR Microspectroscopy and an Artificial Neural Network*. Analytical Chemistry 2009, 81. 2516-2524). Webster et al found that as the parasite matures from its early ring stage to the trophozoite and finally to the schizont stage there is an increase in absorbance and shifting of specific lipid bands.

This work demonstrated the potential of using FTIR spectroscopy as a diagnostic tool for malaria but clearly a synchrotron-based method is not suitable for routine laboratory use.

In particular, malaria detection methods of the prior art have focussed on detection of Hz. However, one of the principal problems with relying solely on the detection of Hz is that early forms of the malaria parasite (the ring stage) have very small amounts of Hz. Thus, many Raman methods of the prior art can optimally detect trophozoites which have large amounts of Hz, however this suffers the drawback that trophozoites are not generally found in peripheral blood.

SUMMARY OF INVENTION

An object of the present invention is to provide a method of malaria detection and quantification suitable for laboratory or field use.

A further object of the present invention is to alleviate at least one disadvantage associated with the related art.

It is an object of the embodiments described herein to overcome or alleviate at least one of the above noted drawbacks of related art systems or to at least provide a useful alternative to related art systems.

In a first aspect of embodiments described herein there is provided a method of detecting malaria comprising the steps of:
  (i) delivering an evanescent IR beam through said ATR substrate in contact with a patient blood sample;
  (ii) detecting IR radiation transmitted from the ATR substrate and producing one or more signals characteristic of one or more lipids in the sample, and
  (iii) processing said one or more signals to identify said one or more lipids and any malaria parasite with which they are associated.

Preferably the processing step includes comparing the one or more signals with a set of reference library spectra of lipids associated with malaria parasites in order to detect matches and quantify said one or more lipids in the sample. The reference library may include a wide range of spectral information including characteristic lipid profiles for lipids associated with each stage of the malaria parasite's life cycle, and control samples of infected and uninfected RBCs. Furthermore, given inherent differences in their characteristics, single cell profiles as well as profiles for broad populations of cells are preferably included in the library.

In contrast to methods of the prior art, the present invention does not rely on detecting Hz. Instead it is focussed on the characteristic spectroscopic lipid signatures expressed by malaria parasites at different stages of their life cycle. The lipid signature detected by ATR-IR is matched with a known spectroscopic lipid signature in a library.

Typically, the patient sample is derived from a small sample of blood removed by pin prick or syringe or the like. The blood may be applied directly to the ATR substrate, but more preferably, the red blood cells are at least partially concentrated by separation from the rest of the blood sample.

The ATR substrate may be of any suitable type known in the technology, but typical substrates include crystals of germanium, zinc selenide or diamond. In a preferred embodiment the ATR substrate for use in the current method is diamond.

The lipids are typically associated with at least one or more of the following: *P. falciparum, P. vivax, P. ovale, P. malariae* and *P. knowlesi*.

The method according to the present invention is relatively sensitive. It is capable of detecting a parasite level of 0.001% (better than 50 parasites/µl blood; p-value=0.0006) or more in a volume of 1 mL blood. More preferably it is capable of detecting a parasite level of at least 100 parasites/µl of sample.

Typically the IR spectroscopy is FTIR, that is, the raw data has been converted into a spectrum by the mathematical process called the Fourier transform. FTIR spectrometers simultaneously collect spectral data in a wide spectral range. The alternative, known as dispersive spectrometry measures intensity over a narrow range of wavelengths at a time but is virtually obsolete.

The processing step of the present invention may be carried out by various techniques. In a preferred embodiment, the processing comprises converting the ATR-IR spectrum into a second derivative, then applying a partial least squares regression model generated by using a library comprising a calibration set of spectral standards containing mixtures of normal and infected RBC at different ratios.

Any suitable algorithm known in the art may be used to convert the spectrum into a second derivative. This removes baseline offsets and resolve inflection points in the spectral bands. Preferably, the second derivative spectrum is then run through a partial least squares (PLS) regression model generated by using a calibration set of spectral standards containing mixtures of normal and infected RBC at different ratios. However many suitable algorithms other than PLS will be readily apparent to the person skilled in the art.

In a second aspect of embodiments described herein there is provided a system of analysis for diagnosing malaria, the system comprising:
 an ATR substrate for receiving a blood sample,
 an FTIR spectrometer for delivering an evanescent IR beam through said ATR substrate,
 a detector for detecting IR radiation transmitted from the ATR substrate to produce a signal,
 a processor for processing said signal to create an FTIR spectrum,
wherein in use an FTIR spectrum of a blood sample is compared with a library of known spectroscopic signatures of lipids associated with malaria parasites to identify matches.

The method and system of the present invention may thus be associated with a software platform that submits the results of ATR-IR to comparison with a library of ATR-IR results for strains of malaria parasites at different stages of development. The library may be local or remote. For example, a spectrum recorded according to the present invention may be submitted from a remote location to a server for identification of matches between the spectrum and a library of known spectroscopic signatures of lipids associated with any malaria parasites in the RBC.

The method or system of the present invention may be used in combination with multivariate statistics or neural network methods to identify the malarial strain associated with the spectroscopic signature of a lipid in the blood sample. Neural networks are computational models that are capable of machine learning and pattern recognition and are particularly well adapted for classification, including pattern and sequence recognition and fitness approximation.

In another aspect of embodiments described herein there is provided a processor means adapted to operate in accordance with a predetermined instruction set, said apparatus, in conjunction with said instruction set, being adapted to perform the method according to the present invention.

Other aspects and preferred forms are disclosed in the specification and/or defined in the appended claims, forming a part of the description of the invention.

In essence, embodiments of the present invention stem from the realization that parasite-specific lipid profiles could be used to detect and identify specific strains of malarial infection. This is a significant deviation from the wisdom of the prior art which focuses on the parasite-specific nature of hemozoin production, particularly detection of hematin (monomeric precursor) or hemozoin.

Advantages provided by the present invention comprise the following:
 detection and quantification of malaria parasites can be rapidly carried out,
 can detect the early stages of the malaria parasite life cycle;
 does not rely on detecting Hz and be used to detect forms of the malaria parasite such as ring and gametocytes that have small, or negligible quantities of Hz;
 no cell counting or chemical treatment is required;
 sample preparation time is minimal (<3 mins per sample);
 the method is simple and inexpensive;
 high sensitivity—a parasite level of 0.001% (better than 50 parasites/µl blood; p-value=0.0006) in a volume of 1 mL blood is required;
 the amount of patient blood required is minimal (approx 10 µl)—a suitable amount can be obtained by pin-prick (which takes approx. 25 µl);
 avoids bias and errors associated with human interpretation.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present application may be better understood by those skilled in the relevant art by reference to the following description of embodiments taken in conjunction with the accompanying drawings, which are given by way of illustration only, and thus are not limitative of the disclosure herein, and in which.

DETAILED DESCRIPTION

The present invention will be illustrated with reference to the experimental methods described below.

Figure 8:
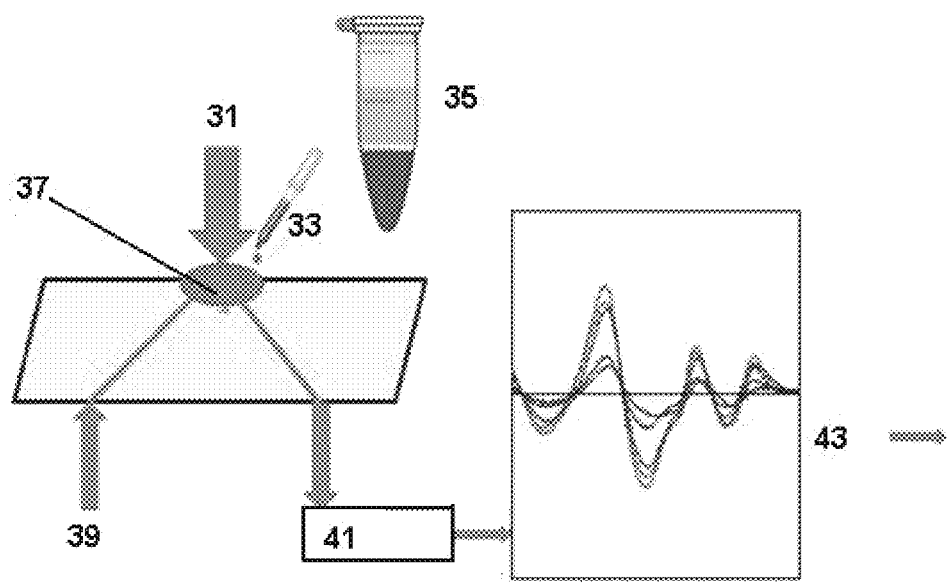
FIG. 8 illustrates a system according to the present invention for ATR-FTIR. The system includes a loading jig (31) for pipette (33) based loading of about 10 µl of RBCs, separated from a whole blood sample by centrifugation in an Eppendorf tube (35). The RBCs are loaded onto an ATR substrate in the form of a diamond crystal (37). An evanescent IR beam (39) is generated by an FTIR spectrometer and imposed on the diamond crystal (27) loaded with the RBC sample. A detector (41) detects the IR radiation transmitted from the diamond crystal (37) to produce a signal characteristic of one or more lipids present in the RBC sample. The resultant signal is passed on to a processor (43) for comparison with the library of malaria parasite associated lipids for diagnosis and further diagnosis.

A system suitable for performing the method of the present invention was created by combining a standard bench top FTIR spectrometer and a diamond crystal ATR accessory as depicted in FIG. 8.

The ATR technique utilizes the property of total internal reflection to generate an evanescent wave, which penetrates 2 to 3 µm into a sample placed in contact with the crystal face, depending on the wavelength, the refractive indices of the crystal and the sample, and the angle of incidence of the infrared beam.

Typically, a suitable small sample of blood can be removed from a patient by pin prick or syringe or any other convenient method. The blood may be applied directly to the ATR substrate, but more preferably, the red blood cells are at least partially concentrated by separation from the rest of the blood sample. This can be done by any convenient means such as centrifugation. The centrifugation step could be carried out in the field using battery driven micro-centrifuges in an Eppendorf tube.

An aliquot of packed RBCs in methanol is placed on the diamond window of the ATR accessory and rapidly dried with a blow dryer (1 minute). While other solvents are also suitable, methanol is particularly preferred because it facilitates the high sensitivity achieved with the ATR-FTIR approach (see below).

The whole process of sample deposition and spectral recording is rapid, and can take less than 3 minutes using a single ATR element. An algorithm converts the spectrum into a second derivative to remove baseline offsets and resolve inflection points in the spectral bands. The second derivative spectrum is then run through a partial least squares regression model generated by using a calibration set of spectral standards containing mixtures of normal and infected RBC at different ratios.

Plasmodium Culture and Gametocyte Enrichment

*Plasmodium falciparum* parasites (3D7 strain) were maintained as previously described (Foley et al, *Photoaffinity labeling of chloroquine-binding proteins in Plasmodium falciparum*. J Biol Chem 1994, 269. 6955-61). Briefly, parasites were maintained in O type human RBCs (sourced from the Australian Red Cross Blood Bank) and cultured in RPMI-HEPES medium supplemented with 5% human serum and 0.25% Albumax. Parasites were synchronized to ring stages by sorbitol lysis (C. Lambros, J. P. Vanderberg, Synchronization of *Plasmodium falciparum* erythrocytic stages in culture. *J Parasitol* 1979, 65. 418-20.) High parasitemia ring stage cultures were obtained by seeding uninfected RBCs with purified schizont stage parasites and allowed to reinvade under shaking conditions overnight, reducing multiple infections. Parasitemias were calculated by Giemsa stained thin blood films, a minimum of 10 fields of view were counted for each culture.

Accurate cell counts were obtained for uninfected and parasite infected RBCs through counting on a hemocytometer. The dilutions were calculated and samples prepared by diluting parasite-infected cultures with uninfected RBCs to obtain the desired dilution. All dilutions were performed in complete culture media, samples were then washed once in 1×PBS, prior to fixation with cold methanol (EMPARTA ACS, Merck) on ice (<0° C.) and mixed thoroughly by pipetting. Samples were stored at 4° C. until analyzed.

Parasitemia Series

A series of infected methanol-fixed RBCs with cultured parasites at different stages including rings, trophozoites, gametocytes at a range of parasitemia percentages (Table 1) were used to establish the PLS calibration models. Uninfected methanol-fixed RBCs were used as the control (0% parasitemia).

TABLE 1

Parasitemia percentages of *P. falciparum*-infected RBCs at different stages.

| Intra-Erythrocytic Stages | Parasitemia series (%) |
|---|---|
| Rings | (a) 0.5, 1, 2.5, 5, 10, 15, 20, 30 |
| Rings | (b) 0.01, 1.75, 0.1, .08, 0.2, 0.43, 7 |
| Rings (2 series) | (c) 0.001, 0.005, 0.01, 0.05, 0.1, 0.5, 1, 3 |
| Rings (2 series) | (d) 0.00001, 0.00005, 0.0001, 0.0005, 0.001, 0.01, 0.1, 0.5, 1 |

TABLE 1-continued

Parasitemia percentages of *P. falciparum*-infected RBCs at different stages.

| Intra-Erythrocytic Stages | Parasitemia series (%) |
|---|---|
| Trophozoites | 0.5, 1, 2.5, 5, 10, 20, 40, 50, 60, 80 |
| Gametocyte | 0.09, 0.3, 0.18, 0.3, 0.75, 1.25, 2.5, 5, 10, 20, 40, 80 |

Equipment & Spectral Data Acquisition (ATR-FTIR Measurements)

A Bruker model EQUINOX 55-(Bruker Optic, Ettingen, Germany) FTIR spectrometer fitted with a $N_2$-cooled mercury-cadmium-tellurium (MCT) detector and a golden gate diamond ATR accessory (Specac limited, Orpington, Kent, UK) was used for spectral acquisition. The Bruker system was controlled with an IBM-compatible PC running OPUS version 6.0 software.

For each sample spectra 200 µL of the packed fixed cells were placed on the diamond cell and air-dried with a blow dryer. Spectra were collected with a spectral resolution of 8 $cm^{-1}$ and 32 co-added interferograms ratioed against a clean diamond background. For each sample deposit, 3-5 replicate spectra were recorded to assess precision and ensure the reproducibility of each sample spectrum.

Data Pre-Processing.

Pre-processing of the spectral data was performed in OPUS-(Bruker Optic, Ettingen, Germany) and the Unscrambler X (Version 10.0.1, Camo, Norway) software packages. For optimal modeling, raw spectra were vector normalized and the second derivative calculated using the Savitzky-Golay algorithm with 9 smoothing points.

Results and Discussion

Fixative Selection Study

The following describes a preliminary study that was carried out to confirm the application of the method of the present invention. The aim was to optimize fixative types and explore spectral variations during storage times. Ethanol, methanol and formaldehyde fixatives were examined in the study. It was found that methanol is a preferred fixative for the ATR measurement according to the present invention as it gives more robust spectra (i.e. less variation during the storage time) and the cells are easily separated from fixative without centrifuging. Another advantage of methanol is that it evaporates rapidly under a blow dryer and leaves no chemical residues. Air-drying or fixing cells with glutaraldehyde does not achieve the same sensitivity and accurate quantification. The methanol may also assist in forcing dissolved lipids to the surface of the ATR crystal especially when under pressure from the sample-clamping device.

It has been calculated that the ATR method according to the present invention can be used to detect lipid residues and Hz deposits from as few as approximately 100 parasites on the ATR diamond crystal face at 0.00001% parasitemia.

Spectral Precision/Reproducibility

Replicate spectra (30 in total from 6 sample deposits×5 spectra per deposit) were obtained from all RBC samples to ensure that representative ATR-FTIR spectra were collected after the sample was air-dried.

After pre-processing (normalization and derivative calculation) statistical tests were performed over the range of replicate spectra (600-4000 $cm^{-1}$) using Unscrambler X software. The descriptive statistics data including variance and standard deviations were used to assess the reproducibility of the IR spectra. As an example the replicate spectra (30 replicates) of the control sample showed a mean absorbance variance of 0.0005. This confirmed the applicability of the method used for deposition and drying of the sample deposit on the diamond crystal face and indicated that the spectra of the dried sample deposits are robust and reproducible.

Overlaid Average Spectra

Figure 1:
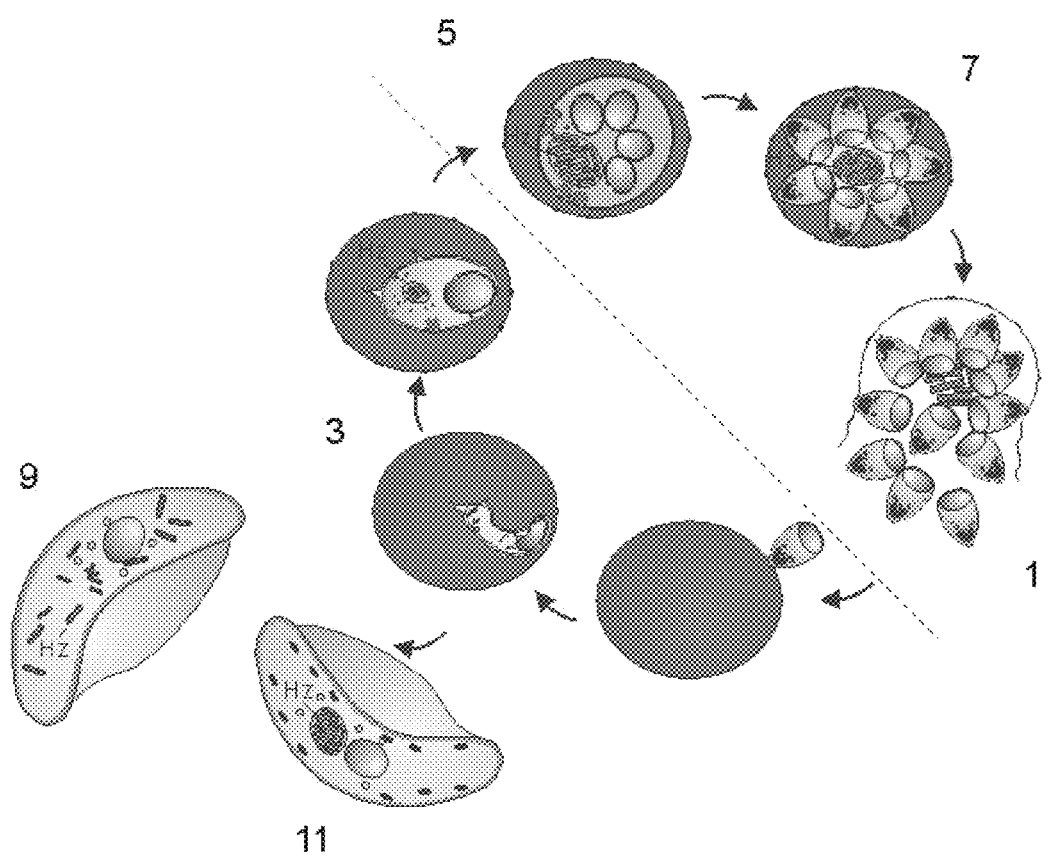
FIG. 1 is a diagram illustrating the asexual and sexual phases of the malaria parasite in the RBC. Merozoites (1) invade RBCs and develop through the ring (3), trophozoite (5) (growing) and schizont (7) (dividing) stages. Some parasites differentiate to form male (9) and female (11) gametocytes that are capable of transmission to mosquitoes. Digestion of haemoglobin leads to the accumulation of Hz. Only ring stage parasites (3) and late gametocytes (9, 11) are present in the blood circulation.
Figure 2A:
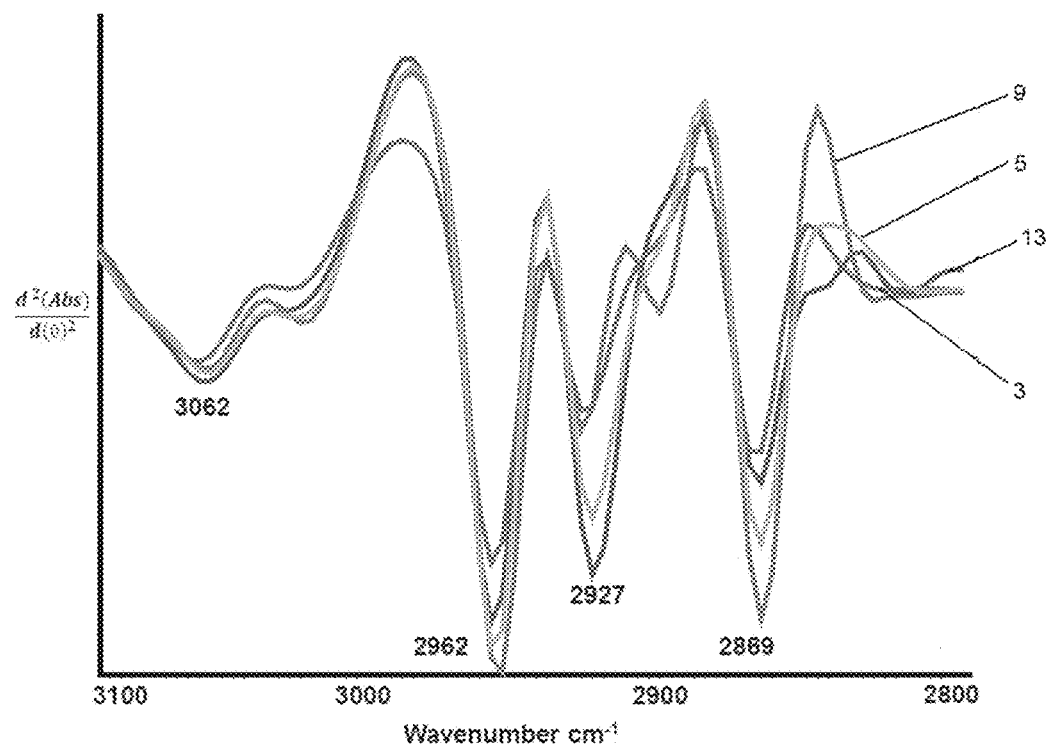
FIGS. 2A and 2B illustrate ATR-FTIR average 2nd-derivative spectra for infected RBCs (Ring, (3) Trophozoite (5), and Gametocyte (9) stages of parasite) and uninfected RBCs (13) (control) of the C—H stretching region (FIG. 2A) and the Hz band marker range (FIG. 2B).
Figure 2B:
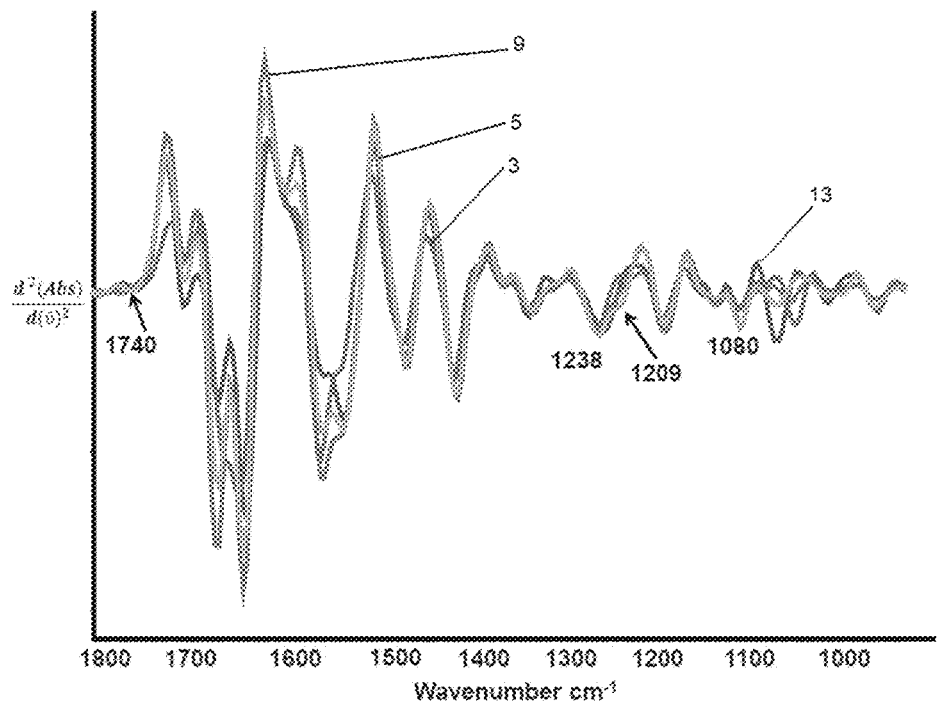

Replicate second derivative spectra from each stage of the parasites life cycle at different parasitemia percentages were averaged (using reduced-average option in Unscrambler-X software) and overlaid (FIG. 2).

Replicate ATR-FTIR spectra from different stages of parasite infected RBCs with the highest available parasitemia percentages [i.e. ring (30%), trophozoite (80%), gametocyte (40%) as well as control (0%) samples] were obtained. FIG. 2 shows the averaged second-derivative overlaid spectra of the C—H stretching region (3100-2800 $cm^{-1}$) as well as the 1800-900 $cm^{-1}$ region highlighting the important Hz marker bands for infected RBCs from different parasite stages.

In the second derivate spectra the absorbance maxima become minima, therefore, in FIG. 2 the positive intensities for absorbance spectra become negative for second-derivative spectra. The CH stretching region (3100-2800 cm−1) is optimally diagnostic for different stages of the parasite as previously shown with synchrotron FTIR spectroscopy (Webster et al, Analytical chemistry 2009, 81. 2516-2524.)

There is also evidence for contributions from nucleic acids as evidenced by the phosphodiester marker bands including the asymmetric stretch at 1241 $cm^{-1}$ and the symmetric stretch at 1095 $cm^{-1}$. The C—O stretching vibration from the propionate group from Hz expected around 1208-1215 $cm^{-1}$ is observed as a shoulder feature in the second derivative spectra of trophozoites and to a lesser extent in the gametocytes. In terms of diagnostic capability use of the CH stretching region was found to achieve a higher sensitivity compared to the 1800-950 $cm^{-1}$ region and a combination of both regions.

Principal Component Analysis (PCA)

PCA was performed on all the replicate RBC samples from individual stages of the parasite life cycle following spectral data pre-processing. PCA is one of the most powerful exploratory tools for large data set analysis. PCA reduces the dimensionality of the data set by decomposing the data set into a signal and noise part by finding linear combinations of the original variables. PCA was applied to second-derivative ATR-FTIR spectra from infected RBCs including the ring trophozoite and gametocyte stages as well as the control samples (uninfected RBCs) with the aim of assessing spectral variance across a sub-population of cells.

Figure 3A:
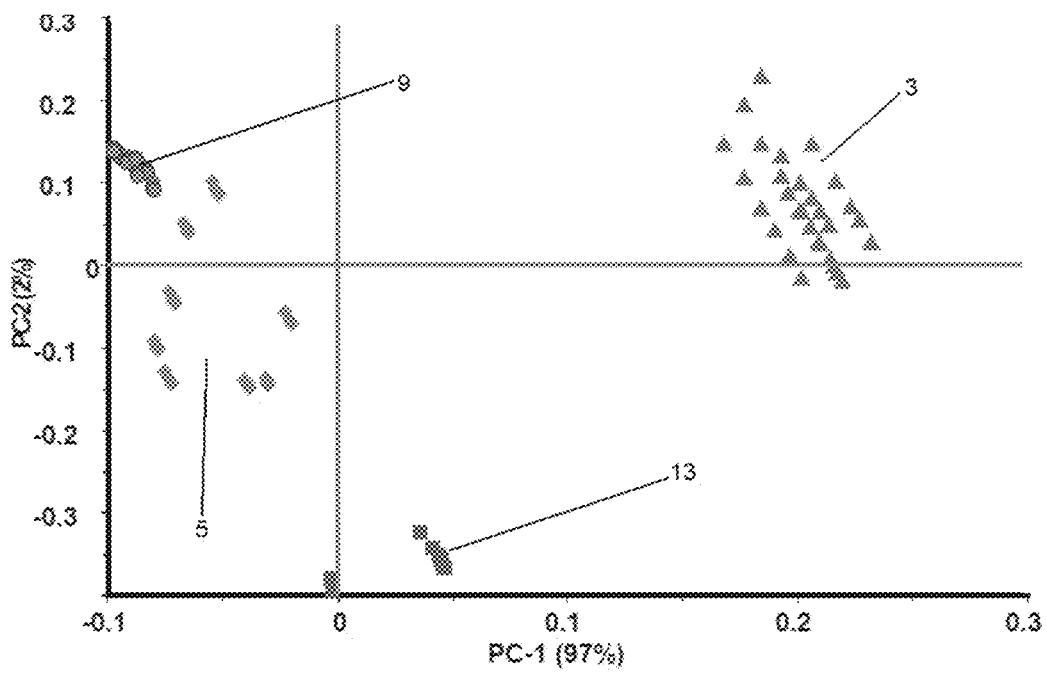
FIGS. 3A and 3B illustrate a PCA Scores Plot along PC1 and PC2 of Control (C), Rings (R), Trophozoite (T) and Gametocytes (G) affected RBC data sets (FIG. 3A) and a PC1 correlation Loadings Plot after a second derivative function was applied to the C—H stretching region (3100-2800 cm−1) (FIG. 3B).

FIG. 3A indicates a clear differentiation and sample grouping for the different stages of parasitemia (i.e. R, T & G) from infected RBCs compared to the control (C) in the C—H stretching region. Ring stage parasites that are to the right of the Scores Plot have a large positive PC1 value compared to all other stages indicating significant differences in the lipid composition compared to the other stages. The linear sub-groupings observed in the clusters arise from the fact that a series of concentrations were used as input data into the PCA. In the ring stage four independent series were included in the PCA model.

Figure 3B:
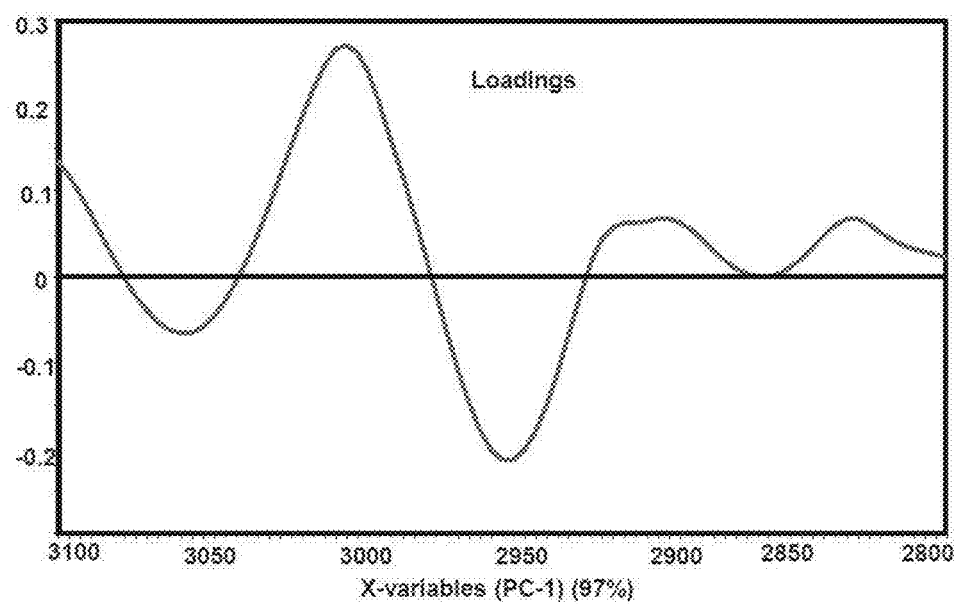

FIG. 3B shows the Loadings Plot for PC1, which displays negative loadings associated with vibrational modes of lipid in the regions of 2888-2880, 3060-2950 $cm^{-1}$ as expected from previous findings (Webster et al, Analytical chemistry 2009, 81. 2516-2524.)

PCA analysis was also applied to the 1800-1000 cm$^{-1}$ region for all stages where the Hz bands are expected (~1712, 1664, and 1209 cm$^{-1}$) (data not shown). However, only a good, rather than excellent separation of the trophozoites and gametocytes from the control was achieved.

The ring stage parasites could not be as definitively separated from the other groups when using this spectral window because the rings only have very small amounts of Hz. The definitive separation in the PCA Scores Plot along with the linearity observed in the sub-groupings because of the different percentages of parastemia demonstrates that the CH stretching region (3100-2800 cm$^{-1}$) is ideal for PLS prediction models.

ATR-FTIR Sensitivity Using PCA Analysis

Figure 4A:
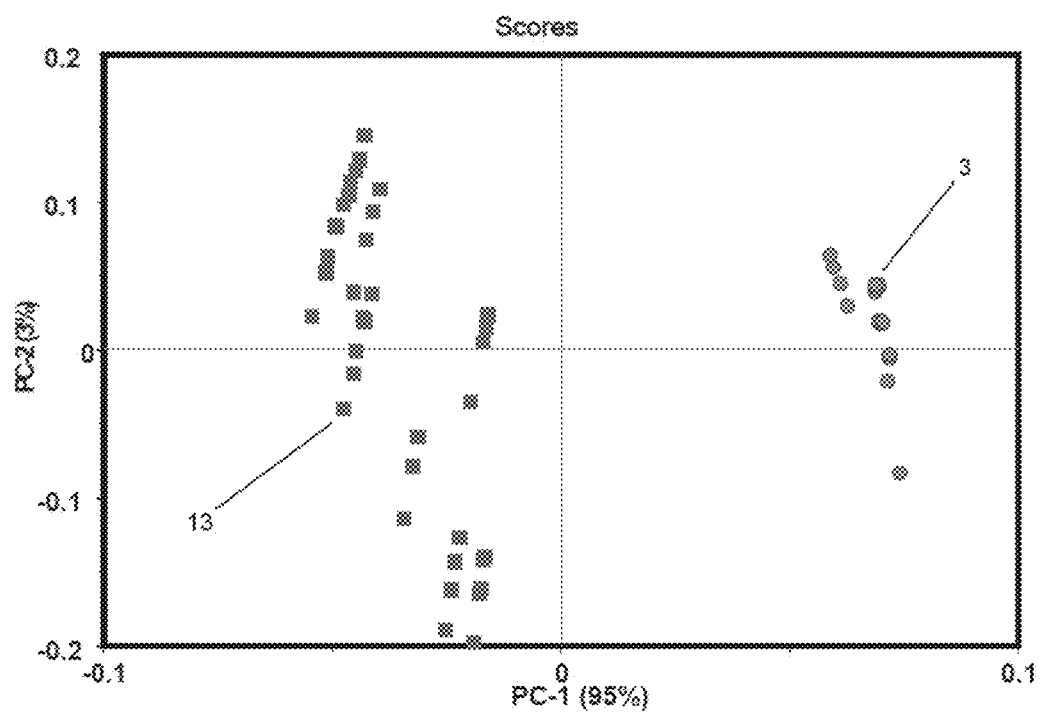
FIGS. 4A and 4B illustrate a PCA Scores Plot (FIG. 4A) and the PC1 correlation Loadings Plot (FIG. 4B) along PC1 and PC2 of Control—0% (13) & Rings 0.00001% (3), after a second derivative function was applied to the C—H stretching region (3100-2800 cm−1).
Figure 4B:
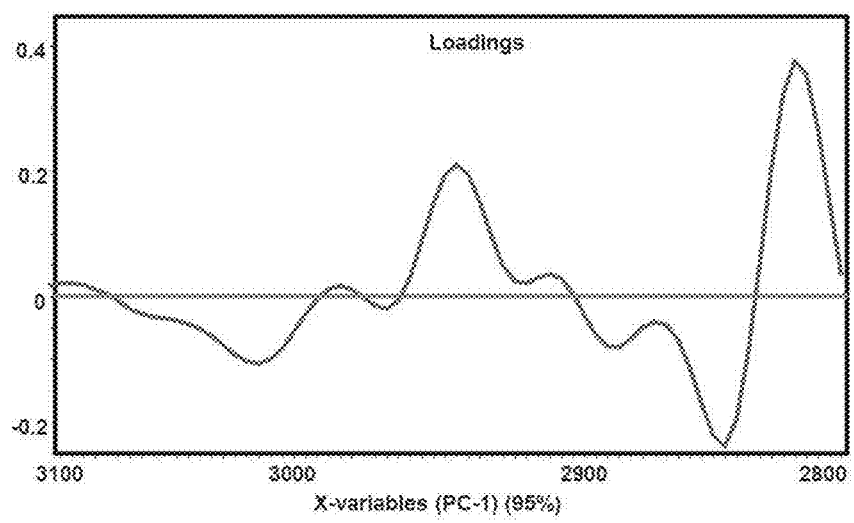

In order to examine the sensitivity of the ATR-FTIR to differentiate parasitemia at very low levels, PCA analysis was applied to the second derivative spectra at the lowest % parasitemia in the sample series for both rings & trophozoites versus control (as 0%). FIG. 4 shows an example of the PCA analysis at 0.00001% parasitemia for rings versus control in the C—H stretching region (3100-2800 cm-1).

In FIG. 4 the Scores Plot indicates a good separation or grouping of rings at 0.00001% parasitemia (the lowest concentration prepared in the ring series) versus control. The Loadings Plot for PC1 shows strong negative loadings in the lipid band regions of 2854, 2954-2944, 2993 and 3063 cm$^{-1}$.

Similar analysis was also performed for the gametocyte and trophozoite series at 0.09 and 0.5% (the lowest concentration available) respectively versus control, which exhibited an excellent separation between the gametocytes, trophozoites and the controls. The results confirm the ability of ATR-FTIR to detect parasitemia levels down to 0.00001%. The same type of PCA analysis was performed in the Hz region (1800-900 cm$^{-1}$), however, no separation was observed indicating the Hz region is ineffective for diagnosing low levels of parasitemia.

PLS Models

Partial least squares (PLS) regression is a statistical method that develops a linear regression model by projecting the predicted variable (% parasitemia) and the observable variable (spectra) onto a new multidimensional space.

For the ring stage parasitemia three PLS models were constructed for three ranges of parasitemia (at the ring stage) from 3 independent trials namely model 1 (10-30%), model 2 (0-5%) and model 3 (0-1%) with the lowest detectable parasitemia at 0.00001%. The PLS model is based on a full cross-validation model where one sample is left out and then the parasitemia of that sample predicted. The corresponding Root Mean Square Error of Validation (RMSEV) and R-squared values for each model are: model 1 (2.50 and 0.94), model 2 (0.32 and 0.95) and model 3 (0.07 and 0.95).

Figure 5:
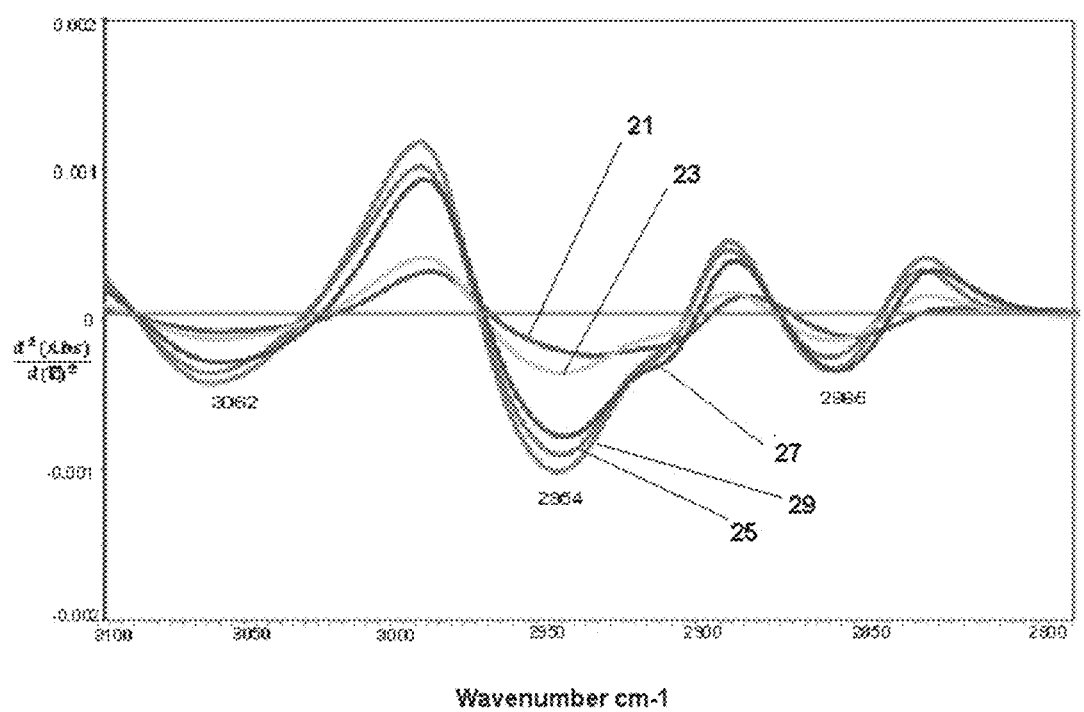
FIG. 5 illustrates spectra of overlaid 2nd derivative spectra showing the type of data used in the generating the calibration models. [Control (21), 0.05% (23), 0.8% (25), 0.5% (27), 3% (29)].
Figure 6A:
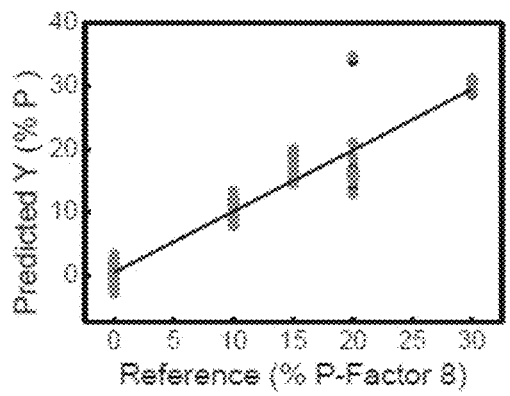
FIGS. 6A, 6B, 6C, 6D, 6E, and 6F illustrate regression plots for the calibration and validation sets for three ranges of early ring stage parasitemia namely model 1 (FIG. 6A: 0, 10, 15, 20 and 30%), model 2 (FIG. 6B: 0, 1, 1.75, 2.5, 3 and 5%) and model 3 (FIG. 6C: 0, 0.00001, 0.005, 0.01, 0.05, 0.1, 0.2, 0.4, 0.5, 0.8 and 1%) along with the corresponding regression co-efficient plots (FIGS. 6D, 6E and 6F respectively) for 8-factors.
Figure 6B:
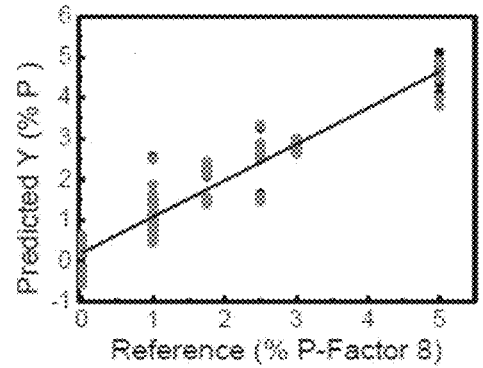
Figure 6C:
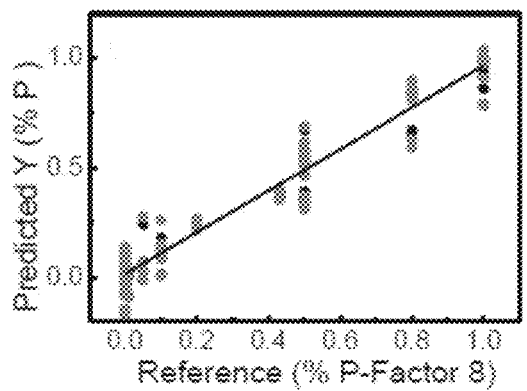
Figure 6D:
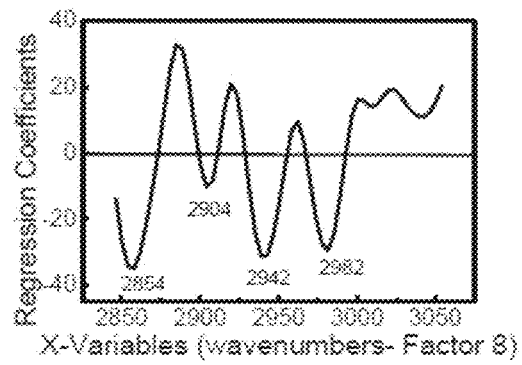
Figure 6E:
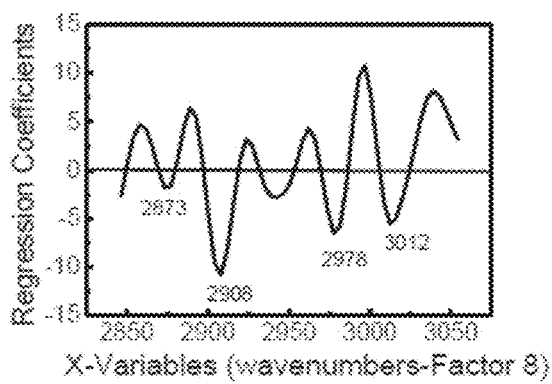
Figure 6F:
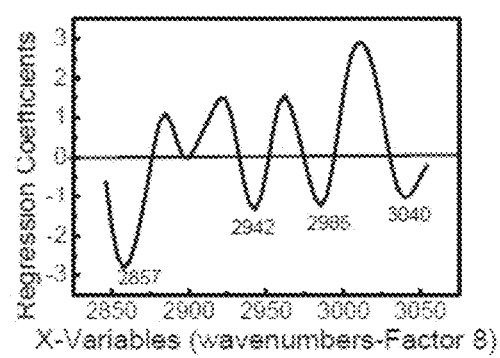

The spectra presented in FIG. 5 show an example set of calibration standards for the ring stage parasites that was used to build the PLS regression model. To generate the final models calibration data from 3 independent trials were incorporated.

The regression plots for the calibration and validation sets are shown in FIG. 6 along with the corresponding regression co-efficient plots for 8-factors. The maxima and minima bands in the regression co-efficient plots show the bands that are important in generating the linearity in the model. These correspond to the major bands associated with the lipid CH stretching vibrations (FIG. 6). Thus, the linearity of the model is based on real spectral changes and not spectral artifacts such as baseline modulations or noise. It was found that the best predictions were obtained when using the lipid CH stretching region (3100-2800 cm-1) as opposed to the 1800-900 cm-1 region, where the majority of bands are present.

Earlier studies have also reported unique lipids associated with the malaria parasite. Studies have shown that neutral lipids accumulate in the digestive compartment and in neutral lipid bodies during parasite development (Jackson et al, Food vacuole-associated lipid bodies and heterogeneous lipid environments in the malaria parasite, *Plasmodium falciparum. Molecular microbiology* 2004, 54. 109-122; Pisciotta et al, The role of neutral lipid nanospheres in *Plasmodium falciparum* haem crystallization. *Biochem. J* 2007, 402. 197-204; and Ambele & Egan, Neutral lipids associated with haemozoin mediate efficient and rapid β-haematin formation at physiological pH, temperature and ionic composition. *Malaria Journal* 2012, 11. 337.)

Images of parasites at the ring stage show small Hz crystals surrounded by neutral lipid spheres inside the digestive vacuole compared to a thinner rim of lipids that surrounds a much larger Hz crystal at the later trophozoite stage. Jackson et al (*Molecular microbiology* 2004, 54. 109-122) demonstrated that neutral lipid bodies contain di- and triacylglycerols and hypothesized that these structures act as storage compartments for lipid by-products formed by phospholipid digestion in the parasite's digestive vacuole. The Hz aliphatic and aromatic CH vibrations also contribute to this lipid spectral region enhancing the overall sensitivity of the technique.

Using the same method for each series of infected RBCs at different stages and percentages of parasitemia, a range of optimum regression models were obtained for both lipid and Hz band ranges with the minimum number of factors and highest model fitness. Results indicated that spectral pre-processing and removal of outliers improved the correlation coefficient between predicted and measured values at lower factors which gives the optimized model with minimum error to be considered as the "best" theoretical fit. The results with second derivatives also indicated further improvement because lower factors were required to achieve high correlation coefficients.

In addition to the above final models from large datasets, a summary of the results from optimum PLS models at C—H stretching region on RBCs of different parasitemia series and at different stages of parasitic life cycle are given in Table 2. It summarizes all the prediction models applied to the ATR-FTIR spectra of ring, trophozoite and gametocytes series as well as combinations of all the series from different stages of parasitemia after the data pre-processing was applied to each model.

TABLE 2

Summary of optimum PLS models at C—H stretching region (3100-2800 cm$^{-1}$) on parasite (P) series: rings (R), trophozoites (T), gametocytes (G) & control (C) and combined series from R, T, G & C.

| P-Type & series | PLS-Conc. Range (% P) | Range of R-squared Factor 1 to 7 | Range of RMSEP* Factor 1 to 7 |
| --- | --- | --- | --- |
| R (d) | 0-0.0001 | 0.54-0.32 | 0.00025-0.00027 |
| R (d) | 0-0.00005 | 0.83-0.52 | 0.00008-0.000012 |
| R (c) | 0-0.1 | 0.993-0.397 | 0.003-0.028 |
| R (a, b) | 0-5 | 0.99-0.21 | 0.16-1.55 |
| R (c) | 0-7 | 0.970-0.153 | 0.1590.858 |
| R (c) | 5-10 | 0.991-0.151 | 0.175-1.73 |
| R (a, c) | 0-10 | 0.988-0.32 | 0.36-2.77 |
| R (a) | 5-30 | 0.997-0.56 | 0.46-6.9 |
| R (a) | 10-30 | 0.998-0.55 | 0.45-6.87 |

TABLE 2-continued

Summary of optimum PLS models at C—H stretching region (3100-2800 cm$^{-1}$) on parasite (P) series: rings (R), trophozoites (T), gametocytes (G) & control (C) and combined series from R, T, G & C.

| P-Type & series | PLS-Conc. Range (% P) | Range of R-squared Factor 1 to 7 | Range of RMSEP* Factor 1 to 7 |
| --- | --- | --- | --- |
| T | 0-5 | 0.976-266 | 0.14-1.6 |
| T | 5-20 | 0.999-0.73 | 0.186-0.7 |
| T | 20-80 | 0.995-0.633 | 1.47-11.04 |
| R (a), T, C | 0-80 | 0.86-0.027 | 8.5-22.1 |
| R (a), G, C | 0-5 | 0.989-0.40 | 0.185-1.4 |
| R (a), T, G, C | 0-5 | 0.96-0.97 | 0.17-0.82 |
| G | 0-5 | 0.91-0.155 | 0.5-1.58 |
| G | 10-80 | 0.93-0.25 | 6.12-20.16 |
| G | 0-5 | 0.996-0.13 | 0.09-1.47 |
| G | 0-5 | 0.999-0.3 | 0.3-11.7 |

*Root Mean Square Error of Predictions

Application of PLS Prediction Models to Unknown/Blind Samples

To assess the applicability and sensitivity of the PLS models, optimized PLS prediction models from low ranges of parasitemia series (0-5, 0-0.1 and 5-10%) were used to predict parasitemia concentration of a series of infected RBCs with rings as unknown or blind samples.

Figure 7:
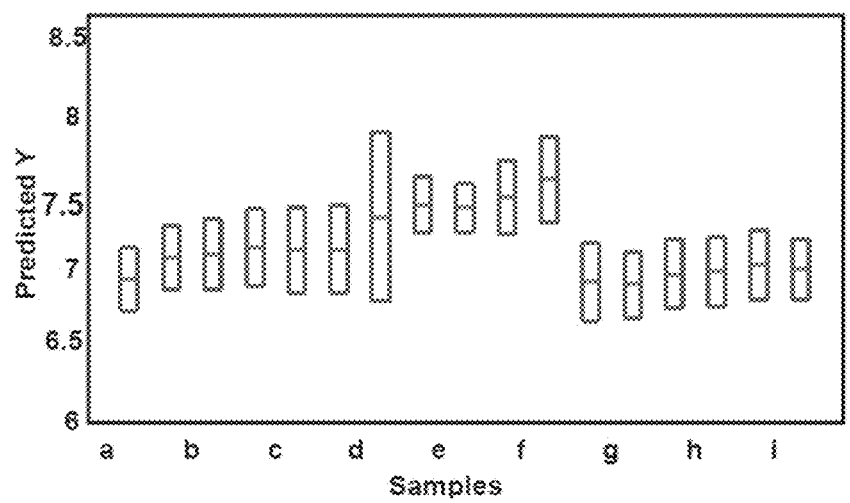
FIG. 7 illustrates example of predictions for unknown samples using PLS models in the range of 5-10% with the average standard error of prediction of 0.08. The predicted values are shown as horizontal lines and the boxes around predicted value indicate the deviation.

The replicate spectra (10-15) of the unknown samples were pre-processed in the same way as the reference samples and used for the PLS prediction. Both PLS models from rings series (with R2>0.99 and RMSE<0.17) as well as from combined spectra from all series were used for predictions. FIG. 7 indicates an example of predictions where ring samples at 7 & 7.4% parasitemia were used as unknown and a PLS model in the range of 5-10% parasitemia was used, the average standard error of the prediction-deviations was 0.08% at factor 1.

More ring samples with parasitemia levels in the range of 0 to 2 were also used as unknowns. The average predicted concentrations of the ring samples were all within 0-2% with average error of 0.2 (Hotelling T$^2$ at 95% confidence limit). Predictions for the unknown samples with <0.1% parasitemia showed an average standard deviation of 0.05.

The reasons for the prediction variation especially at low parasitemia levels could be due to; (i) the varying number of infected cells deposited on the ATR diamond cell that may have caused non-uniformity in lipid distribution in the dried-sample deposits, (ii) varying thickness of the lipid deposit at the crystal surface (iii) the error involved in the sample preparation (e.g. separation and dilution) and the reference method.

Sample uniformity, particle size and consistency in sample thickness on the diamond cell were found to be the most important factors in obtaining consistent spectral acquisition and error reduction for prediction of unknown samples. The detection limit or sensitivity of the predictions was found to be 0.2% within 95% confidence limit.

The experimental results described thus demonstrate the utility of ATR FTIR spectroscopy as a method for rapid detection and quantification of malaria parasite infections.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures.

It should be noted that where the terms "server", "secure server" or similar terms are used herein, a communication device is described that may be used in a communication system, unless the context otherwise requires, and should not be construed to limit the present invention to any particular communication device type. Thus, a communication device may include, without limitation, a bridge, router, bridge-router (router), switch, node, or other communication device, which may or may not be secure.

Various embodiments of the invention may be embodied in many different forms, including computer program logic for use with a processor (e.g., a microprocessor, microcontroller, digital signal processor, or general purpose computer and for that matter, any commercial processor may be used to implement the embodiments of the invention either as a single processor, serial or parallel set of processors in the system and, as such, examples of commercial processors include, but are not limited to Merced™, Pentium™, Pentium II™, Xeon™, Celeron™, Pentium Pro™, Efficeon™, Athlon™, AMD™ and the like), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof.

In an exemplary embodiment of the present invention, predominantly all of the communication between users and the server is implemented as a set of computer program instructions that is converted into a computer executable form, stored as such in a computer readable medium, and executed by a microprocessor under the control of an operating system.

Computer program logic implementing all or part of the functionality where described herein may be embodied in various forms, including a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML. Moreover, there are hundreds of available computer languages that may be used to implement embodiments of the invention, among the more common being Ada; Algol; APL; awk; Basic; C; C++; Conol; Delphi; Eiffel; Euphoria; Forth; Fortran; HTML; Icon; Java; Javascript; Lisp; Logo; Mathematica; MatLab; Miranda; Modula-2; Oberon; Pascal;

Perl; PL/I; Prolog; Python; Rexx; SAS; Scheme; sed; Simula; Smalltalk; Snobol; SQL; Visual Basic; Visual C++; Linux and XML.) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g, a RAM, ROM, PROM, EEPROM, or Flash-Programmable RAM), a magnetic memory device (e.g., a diskette or fixed disk), an optical memory device (e.g., a CD-ROM or DVD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and inter-networking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality where described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL). Hardware logic may also be incorporated into display screens for implementing embodiments of the invention and which may be segmented display screens, analogue display screens, digital display screens, CRTs, LED screens, Plasma screens, liquid crystal diode screen, and the like.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

"Comprises/comprising" and "includes/including" when used in this specification is taken to specify the presence of stated features, integers, steps or components but does not preclude the presence or addition of one or more other features, integers, steps, components or groups thereof.

Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

The invention claimed is:

1. A method of detecting parasitemia with an ATR-FIR spectrometer comprising:
    (i) delivering an evanescent IR beam using an ATR substrate of an ATR-FTIR spectrometer in contact with a patient sample, wherein the patient sample is dried onto the ATR substrate;
    (ii) detecting IR radiation transmitted from the AIR substrate to produce a spectrum of the patient sample;
    (iii) processing one or more signals in the spectrum to identify any parasite; and
    (iv) determining a parasitemia level of the patient sample using one or more signals in the spectrum.

2. The method according to claim 1 wherein the parasitemia level is ≥100 parasites/µl of sample.

3. The method according to claim 1 wherein the parasitemia level is ≥50 parasites/µl of sample.

4. The method of claim 1, wherein the processing comprises converting the spectrum into a second derivative, then applying a partial least squares regression model generated by using a library comprising a calibration set of spectral standards containing mixtures of normal and infected patient samples at different ratios.

5. The method of claim 4, further comprising transmitting the spectrum from a remote location to a server, and wherein the processing is performed at the server.

6. The method of claim 1, wherein the processing of the signal is performed via execution by the processor of a predetermined instruction set stored in a computer readable medium.

7. The method of claim 1, further comprising fixing the sample in methanol.

8. The method of claim 7, further comprising drying the sample using a heat source.

9. The method of claim 1, wherein the one or more signals in the spectra are one more signals in the spectra at 2850, 2854, 2873, 2904, 2908, 2942, 2978, 2982, 2985, 3012 or 3040 cm-1.

10. The method of claim 1, wherein the one or more signals in the spectrum comprise different spectra at different parasitemia levels.

11. The method of claim 1, wherein the one or more signals in the spectrum comprise at least one signal at 2854, 2904, 2942 or 2982 cm-1 to quantify a parasitemia level between 10-30%.

12. The method of claim 1, wherein the one or more signals in the spectrum comprise signals at 2854, 2904, 2942 and 2982 cm-1 to quantify a parasitemia level between 10-30%.

13. The method of claim 1, wherein the one or more signals in the spectra comprise at least one signal of at 2873, 2908, 2978 or 3012 cm-1 to quantify a parasitemia level between 0-5%.

14. The method of claim 1, wherein the one or more signals in the spectrum comprise signals at 2873, 2908, 2978 and 3012 cm-1 to quantify a parasitemia level between 0-5%.

15. The method of claim 1, wherein the one or more signals in the spectrum comprise at least one signal of at 2857, 2942, 2985 or 3040 cm-1 to quantify a parasitemia level between 0-1%.

16. The method of claim 1, wherein the one or more signals in the spectra comprise signals at 2857, 2942, 2985 and 3040 cm-1 to detect the presence of any parasitemia.

17. A method, comprising:
with a processor, executing an instruction set stored in a non-transitory computer readable storage medium, the instruction set including instructions to compare one or more spectral signals characteristic of an infected patient sample to detect matches and quantify a parasitemia level using different wavenumber values or absorbance values for different infection levels.

18. The method of claim 17, wherein the one or more signals are spectral bands at 2850, 2854, 2873, 2904, 2908, 2942, 2978, 2982, 2985, 3012 or 3040 cm-1.

19. The method of claim 17, wherein the one or more signals comprise different spectra at different parasitemia levels.

20. A system of analysis for diagnosing infection, the system comprising:
an ATR substrate for receiving a patient fluid sample;
an FTIR spectrometer configured to generate an evanescent wave that extends into sample using the ATR substrate;
a detector for detecting IR radiation transmitted from the ATR substrate to produce a signal; and
a processor configured to process the signal to create an FTIR spectrum of the patient sample and determine an infection level using different wavenumber values for different infection levels.

21. The system of claim 20, wherein the processor is located in a server and the AIR substrate, FTIR spectrometer and detector are at a remote location from the processor.

22. A method of detecting parasitemia with an ATR-FTIR spectrometer comprising:
(i) delivering an evanescent IR beam using an AIR substrate of an ATR-FTIR spectrometer in contact with a patient sample, wherein the patient sample is dried onto the ATR substrate;
(ii) detecting IR radiation transmitted from the ATR substrate to produce a spectrum of the patient sample;
(iii) transmitting the spectrum from a remote location to a server;
(iv) processing one or more signals in the spectrum to identify any parasite; and
(iv) determining a parasitemia level of the patient sample using one or more signals in the spectrum.

23. The method of claim 22, wherein processing one or more signals in the spectrum is performed on the server.

24. The method of claim 22, wherein determining the parasitemia level is performed on the server.

* * * * *